United States Patent [19]

Schirmer et al.

[11] Patent Number: 5,015,762
[45] Date of Patent: * May 14, 1991

[54] ARALKYLPHENYLUREAS AND HERBICIDES CONTAINING THESE

[75] Inventors: Ulrich Schirmer, Heidelberg; Wolfgang Rohr, Wachenheim; Bruno Wuerzer, Otterstadt, all of Fed. Rep. of Germany

[73] Assignee: BASF Aktiengesellschaft, Ludwigshafen, Fed. Rep. of Germany

[ * ] Notice: The portion of the term of this patent subsequent to Dec. 27, 2000 has been disclaimed.

[21] Appl. No.: 268,120

[22] Filed: May 28, 1981

[30] Foreign Application Priority Data

Jun. 2, 1980 [DE] Fed. Rep. of Germany ....... 3020969

[51] Int. Cl.$^5$ ........................................... C07C 259/00
[52] U.S. Cl. ................................... 560/313; 544/58; 544/4; 544/163; 544/165; 546/226; 548/538; 560/9; 560/13; 560/14; 560/22; 560/34; 562/426; 562/430; 562/432; 562/439; 564/48; 564/49; 564/52; 564/53; 564/54; 558/414; 71/88; 71/90; 71/94; 71/95; 71/98; 71/100; 71/103; 71/104; 71/105; 71/107; 71/111; 71/120
[58] Field of Search ...................... 71/120, 88, 90, 94, 71/95, 98, 100, 103, 104, 105, 107, 111, 115; 564/48, 49, 52, 53, 54; 260/453 RW, 454, 456 A, 465 D, 239 A, 239 B; 560/9, 13, 14, 27, 34; 562/426, 430, 432, 439; 544/58, 4, 163, 165; 546/226; 548/538

[56] References Cited

U.S. PATENT DOCUMENTS

| | | | |
|---|---|---|---|
| 3,332,981 | 7/1967 | Shultis et al. | 564/52 X |
| 3,683,001 | 8/1972 | Knowles | 564/52 X |
| 3,819,697 | 6/1974 | Cross | 564/52 |
| 4,279,637 | 7/1981 | Wu | 564/48 X |
| 4,405,358 | 9/1983 | Schirmer et al. | 71/120 X |
| 4,422,871 | 12/1983 | Schirmer et al. | 71/120 |
| 4,437,880 | 3/1984 | Takahashi et al. | 71/120 |

FOREIGN PATENT DOCUMENTS 40859 12/1981 European Pat. Off. .
2846723 5/1979 Fed. Rep. of Germany .

OTHER PUBLICATIONS

Chemical Senses and Flavour, vol. 4, No. 1, (1979) pp. 35–47.

Primary Examiner—Charles F. Warren
Attorney, Agent, or Firm—Keil & Weinkauf

[57] ABSTRACT

Aralkylphenylureas of the formula

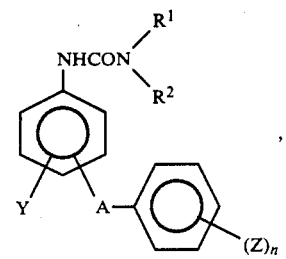

where $R^1$ and $R^2$ are hydrogen, alkoxy or unsubstituted or substituted alkyl, cycloalkyl, alkenyl or alkynyl, or $R^1$ and $R^2$ together are unsubstituted or substituted alkylene which may or may not be interrupted by oxygen or sulfur, Y is hydrogen, alkyl, halogen, alkoxy or haloalkyl, A is unsubstituted or substituted alkylene, Z is hydrogen, alkyl, haloalkyl, alkoxyalkyl, cycloalkyl, aralkyl, aryl, aryloxy, halogen, a $C_4H_4$ chain which is fused to the benzene ring to give a substituted or unsubstituted naphthyl ring, alkoxy, haloalkoxy, alkylthio, thiocyanato, cyano,

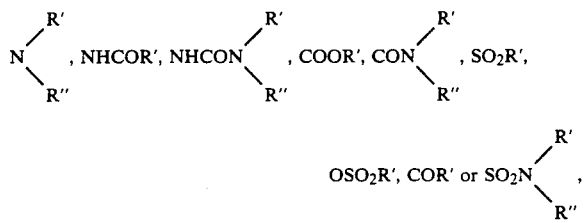

R' and R" being hydrogen, alkyl, alkoxy, alkylthio, cycloalkyl or unsubstituted or substituted phenyl and n is 1, 2, 3 or 4, and herbicides containing these ureas.

7 Claims, No Drawings

ARALKYLPHENYLUREAS AND HERBICIDES CONTAINING THESE

The present invention relates to novel, valuable aralkylphenylureas having a herbicidal action, processes for the preparation of these compounds, herbicides containing these compounds, and methods of control of undesired plant growth by means of these compounds.

It is known from German Laid-Open Application DE-OS 2,846,723 that aralkoxyphenylureas, for example 1-(3-(2-phenylethoxy)-phenyl)-3-methoxy-3-methylurea, have herbicidal properties.

We have found that aralkylphenylureas of the formula

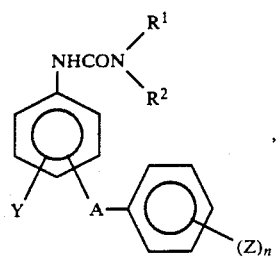

where $R^1$ and $R^2$ are hydrogen, alkoxy or unsubstituted or halogen-, alkoxy- or cyano- substituted alkyl, cycloalkyl, alkenyl or alkynyl, or $R^1$ and $R^2$ together are unsubstituted or alkyl-substituted alkylene which may or may not be interrupted by oxygen or sulfur, Y is hydrogen, alkyl, halogen, alkoxy or haloalkyl, A is unsubstituted or alkyl-substituted alkylene, Z is hydrogen, alkyl, haloalkyl, alkoxyalkyl, cycloalkyl, aralkyl, aryl, aryloxy, halogen, a $C_4H_4$ chain which is fused to the benzene ring to give a substituted or unsubstituted naphthyl ring, alkoxy, haloalkoxy, alkylthio, thiocyanato, cyano,

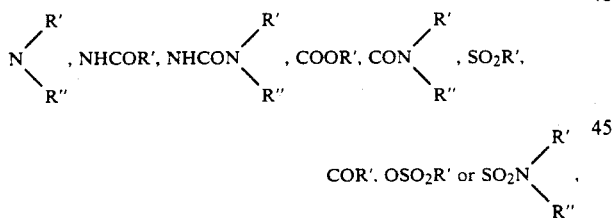

R' R" each, independently of one another, being hydrogen, alkyl, alkoxy, alkylthio, cycloalkyl or unsubstituted or alkyl-, halogen- or alkoxy-substituted phenyl and n is 1, 2, 3 or 4, exert a good herbicidal action on numerous important undesired plants, and are well tolerated by various crops.

Examples of possible meanings of the radicals shown in the general formula are:

$R^1$ and $R^2$ (independently of one another): hydrogen, alkoxy (e.g. methoxy or ethoxy), unsubstituted or halogen-, alkoxy- or cyano-substituted alkyl (e.g. methyl, ethyl, isopropyl, n-propyl, n-butyl, sec.-butyl, tert.-butyl, n-butyl, iso-butyl, sec.-pentyl, 2-chloroethyl, 2-methoxyethyl and 2-cyanomethyl), cycloalkyl, alkenyl or alkynyl (e.g. cyclopropyl, cyclohexyl, sec.-butynyl, propargyl and allyl).

$R^1$ and $R^2$ together: unsubstituted or alkyl-substituted alkylene of 2 to 8 carbon atoms which can be interrupted by oxygen or sulfur (e.g. propylene, butylene, pentylene, hexylene, 1,4-dimethylbutylene, 3-oxapentylene and 3-thiopenylene).

Y: hydrogen, alkyl (e.g. methyl and t-butyl), halogen (e.g. fluorine, chlorine and bromine), alkoxy (e.g. methoxy) and haloalkyl (e.g. trifluoromethyl).

A: unsubstituted or alkyl-substituted alkylene of 1 to 10 carbon atoms (e.g. methylene, methylmethylene, dimethylmethylene, propylene, hexylene, ethylene, methylethylene, methylpropylene, ethylpropylene, butylene, pentylene, methylpentylene, dimethylpropylene, heptylene, ethylbutylene and trimethylpentylene).

Z: hydrogen, alkyl (e.g. methyl, ethyl and t-butyl), haloalkyl (e.g. trifluoromethyl), alkoxyalkyl (e.g. methoxymethyl), cycloalkyl (e.g. cyclohexyl), aralkyl (e.g. benzyl), aryl (e.g. phenyl), aryloxy (e.g. phenoxy), halogen (e.g. fluorine, chlorine, bromine or iodine), a $C_4H_4$ chain which is fused to the benzene ring to give an unsubstituted or substituted naphthyl ring, alkoxy (e.g. isopropoxy and hexoxy), haloalkoxy (e.g. 1,1,2,2-tetrafluoroethoxy), alkylthio (e.g. methylthio), thiocyanato, cyano,

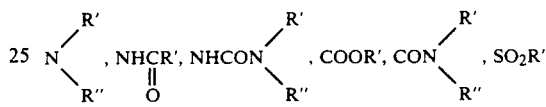

where R' and R" are each, independently of one another, hydrogen, alkyl (e.g. methyl or ethyl), alkoxy (e.g. methoxy or tert.-butoxy), alkylthio (e.g. methylthio), cycloalkyl (e.g. cyclohexyl) or unsubstituted or alkyl-, halogen- or alkoxy-substituted phenyl (e.g. phenyl, 3-chlorophenyl, 4-methylphenyl or 3-methoxyphenyl).

The novel compounds can be prepared by, for example, the following processes:

PROCESS I

An aralkylphenyl isocyanate of the formula

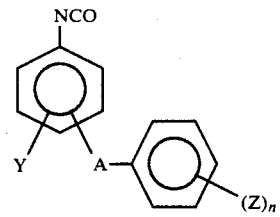

where Y, A and $(Z)_n$ have the above meanings, is reacted with an amine of the general formula

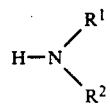

where $R^1$ and $R^2$ are as defined above.

The reaction of the aralkylphenyl isocyanate is carried out with or without a conventional catalyst for isocyanate reactions, for example a tertiary amine (e.g. triethylamine or 1,4-diazabicyclo-(2,2,2)-octane), a nitrogen-containing heterocyclic (e.g. pyridine or 1,2-dimethylimidazole) or an organic tin compound (dibutyltin diacetate or dimethyl-tin dichloride), in the presence or absence of a solvent which is inert under the reaction conditions, for example a hydrocarbon (e.g. naphtha, gasoline, toluene, pentane or cyclohexane), a halohydrocarbon (e.g. methylene chloride, chloroform, dichloroethane, chlorobenzene or o-, m- or p-dichlorobenze), a nitrohydrocarbon (e.g. nitrobenzene or nitromethane), a nitrile (e.g. acetonitrile, butyronitrile or benzonitrile), an ether (e.g. diethyl ether, tetrahydrofuran or dioxane), an ester (e.g. ethyl acetate or methyl propionate), a ketone (e.g. acetone or methyl ethyl ketone) or an amide (dimethylformamide or formamide), at from 0 to 150° C., preferably from 40 to 100° C. (cf. S. Petersen in Methoden der Organ. Chemie, vol. VIII, p. 132, Georg-Thieme-Verlag, Stuttgart, 4th edition (1952)).

PROCESS II

An aralkylaniline of the formula

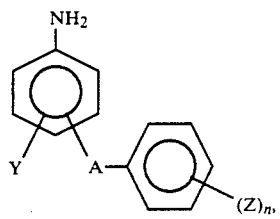

where Y, A and $(Z)_n$ have the above meanings, is reacted with an isocyanate of the general formula $$R^1-NCO,$$

where $R^1$ has the above meanings. This process is carried out like process I and only gives compounds where $R^2$ is hydrogen.

PROCESS III

An aralkylaniline of the formula

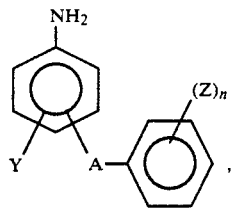

where Y, A and $(Z)_n$ have the above meanings, is reacted with a compound of the general formula

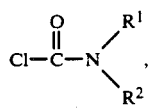

where $R^1$ and $R^2$ are as defined above. The reaction is carried out with or without a suitable solvent (see Process I), in the presence of a conventional acid acceptor, for example an alkali metal hydroxide, carbonate or bicarbonate, an alkaline earth metal oxide, hydroxide, carbonate or bicarbonate, or a tertiary organic base (e.g. triethylamine, pyridine, N,N-dimethylaniline, N,N-dimethylcyclohexylamine, quinoline or tributylamine), at from −20° to 150° C., preferably from 20° to 80° C.

To prepare the aralkylphenyl isocyanates required in Process I, an aralkylaniline of the formula shown under Process II is reacted, by conventional methods, with phosgene (W. Siefken, J. Liebigs Annalen der Chemie 562 (1949), 75 et seq.). To prepare the aralkylanilines required in Process II, a nitrobenzene of the general formula

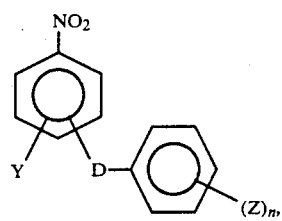

where D is a saturated or unsaturated, unsubstituted or alkyl-substituted alkylene chain, which may or may not be interrupted by a keto group, or D is a keto group, and Y and $(Z)_n$ have the above meanings, is catalytically hydrogenated, using a conventional hydrogenation catalyst (for example palladium on charcoal, platinum sponge or Raney nickel), a suitable solvent, such as a carboxylic acid (e.g. acetic acid), an ether (e.g. tetrahydrofuran) or an alcohol (e.g. ethanol), and, where appropriate, a strong acid (e.g. methanesulfonic acid or sulfuric acid), at from 0° to 150° C. and under a pressure of from 1 to 100 bar (B. R. Baker et al., J. Pharm. Sci. 56(1967), 737–742).

The required nitrobenzenes can be prepared by conventional processes (cf., for example, B. R. Baker et al., loc. cit.; P. Pfeiffer et al., J. Prakt. Chem. 109 (1925), 41; R. Geigy and W. Koenigs, Chem. Ber. 18(1885), 2401–2407; P. Petrenko-Kritshenko, Chem.Ber. 25(1892), 2239–2242).

The Examples which follow illustrate the preparation of the novel aralkylaniline derivatives and of their intermediates.

METHOD A 3-(3-Phenylpropyl)-phenyl isocyanate 170 g of phosgene are dissolved in 200 ml of toluene at −10° C. At the same temperature, 145 g of 3-(3-phenylpropyl)-aniline in 300 ml of toluene are then slowly added dropwise. The mixture is warmed slowly, the introduction of phosgene is started when 60° C. is reached, and the mixture is brought to the boil. After 6 hours, excess phosgene is flushed out with nitrogen and the mixture is distilled. 156 g of 3-(3-phenylpropyl)-phenyl isocyanate, of boiling point 107°–110° C./0.1 mbar, are obtained.

METHOD B 3-(3-Phenylpropyl)-aniline 253 g of 1-phenyl-3-(3'-nitrophenyl)-prop-2-en-1-one are suspended in 2.5 liters of glacial acetic acid. 196 g of concentrated sulfuric acid and 10 g of 10% strength Pd on animal charcoal are added and the mixture is hydrogenated under 1.1 bar hydrogen pressure at 65°–70° C., until no further hydrogen is absorbed. When the mixture has cooled, some of the acetic acid is distilled off, the residue is rendered alkaline with sodium hydroxide solution and extracted by shaking with ether, the organic phase is dried over sodium sulfate and filtered, the solvent is stripped off and the residue is distilled. 150 g of 3-(3-phenylpropyl)-aniline of boiling point 148° C./0.2 mbar are obtained.

The following aralkylanilines can be prepared correspondingly: 3-benzylaniline (melting point 43°–45° C.), 3-(3-(2-chlorophenyl)-propyl)-aniline (boiling point 156°–158° C./0.1 mbar), 3-(3-(4-chlorophenyl)-propyl)-aniline (boiling point 160°–161° C./0.1 mbar), 3-(3-(2-methoxyphenyl)-propyl)-aniline (boiling point 168°–170° C./0.3 mbar), 3-(3-(3-methoxyphenyl)-(propyl)-aniline (boiling point 181°–182° C./0.4 mbar), 3-(3-(3-methylphenyl)-propyl)-aniline (boiling point 142°–145° C./0.01 mbar), 3-(3-(4-methylphenyl)-propyl)-aniline (boiling point 148°–150° C./0.1 mbar), 3-(3-(3-trifluoromethylphenyl)-propyl)-aniline (boiling point 142°–145° C./0.3 mbar), 3-(3-(4-fluorophenyl)-propyl-aniline (boiling point 125°–127° C./0.1 mbar), 3-(3-(4-tert.-butylphenyl)-propyl-aniline (boiling point 180°–185° C./0.4 mbar), 3-(3-(4-phenylphenyl)-propyl)-aniline (melting point 76°–77° C.), 3-(3-(4-ethylphenyl)-propyl)-aniline (boiling point 165°–168° C./0.2 mbar), 3-(3-(3-chlorophenyl)-propyl)-aniline (boiling point 165°–172° C./0.4 mbar), 3-(3-(3-hydroxyphenyl)-propyl)-aniline (melting point 59°–61° C.), 3-(3-(3,4-dimethoxyphenyl)-propyl-aniline (boiling point 195° C./0.15 mbar), 3-(3-(4-methoxyphenyl)-propyl)-aniline (boiling point 176° C./0.1 mbar), 4-(3-phenylpropyl)-aniline (boiling point 156°–157° C./0.4 mbar), 3-(2-methyl-3-phenyl-propyl)-aniline (boiling point 152°–153° C./0.4 mbar), 3-(2-methyl-3-(4-fluorophenyl)-propyl)-aniline, 3-(4-methyl-5-phenyl-pentyl)-aniline (boiling point 177°–179° C./0.3 mbar), 3-(2-ethyl-3-phenyl-propyl)-aniline (boiling point 158°–162° C./0.2 mbar), 4-(3-(4-methylphenyl-propyl-aniline (melting point 53°–56° C.), 3-(3-phenylpropyl)-4-bromoaniline (boiling point 159°–160° C./0.1 mbar), 4-(3-(5-fluorophenyl)-propyl)-aniline (boiling point 146°–147° C./0.1 mbar), 4-(3-(2-methylphenyl)-propyl)-aniline (boiling point 160°–162° C./0.1 mbar), 4-(3-(3-methylphenyl)-propyl)-aniline, 4-(4'-phenyl)-benzylaniline (melting point 105°–107° C.), 4-benzylaniline (melting point 35°–37° C.), 4-(3-(3-methoxyphenyl)-propyl)-aniline (boiling point 178°–180° C./0.1 mbar), 4-(2-phenylethyl)-aniline (melting point 42°–45° C.), 3-(2-phenylethyl)-aniline (melting point 50°–52° C.), 4-(4-phenylbutyl)-aniline (oil), 3-(4-phenylbutyl)-aniline (oil), 3-(3-(2-methylphenyl)-propyl)-aniline (boiling point 150°–153° C./0.2 mbar), 3-(3-(3-phenoxyphenyl)-propyl)-aniline (boiling point 195° C./0.2 mbar), 3-(3-(4-ethoxyphenyl)-propyl)-aniline (boiling point 177° C./0.3 mbar), 3-(3-tetrafluoroethoxy-phenyl)-propyl)-aniline (boiling point 155° C./0.1 mbar), 3-(3-(4-chlorophenyl)-propyl)-aniline (boiling point 150°–154° C./0.1 mbar), 3-(3-(3,4-dichlorophenyl)-propyl)-aniline (boiling point 177°–182° C./0.1 mbar) and 3-(3-(α-naphthyl)-propyl)-aniline.

EXAMPLE 1

11 g of 2,5-dimethylpyrrolidine are added dropwise to a mixture of 23.7 g of 3-(3-phenylpropyl)-phenyl isocyanate and 200 ml of toluene at 0° C. After it has been stirred for 6 hours, the mixture is concentrated and the residue is stirred with petroleum ether. 25.1 g of white crystals of melting point 86°–88° C. are obtained; the product has the following structural formula (active ingredient No. 1).

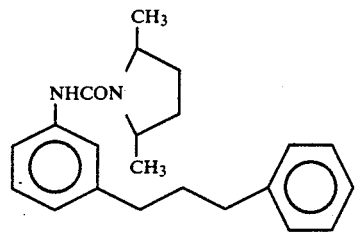

EXAMPLE 2

7.6 g of N-methyl-N-methoxycarbamyl chloride are added dropwise to a mixture of 15 g of 3-(3-(4-chlorophenyl)-propyl)-aniline, 8 g of NaHCO$_3$ and 200 ml of THF at 20° C. and the mixture is stirred overnight. After the solution has been filtered and concentrated, the residue is chromtographed over silica gel, using a mixture of 90 parts of toluene and 10 parts of ethyl acetate. 14.6 g of a product, of melting point 73°–76° C., having the following structural formula are obtained (active ingredient No. 2):

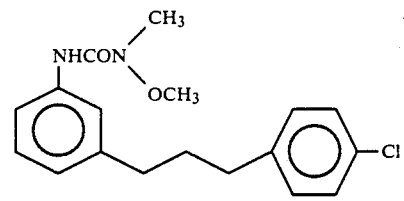

EXAMPLE 3

A mixture of 42.2 g of 3-(3-phenylpropyl)-aniline, 12.2 g of methyl isocyanate, 2 drops of dibutyltin diacetate and 400 ml of THF is left to stand for 4 days at 20° C. and is then concentrated, and the residue is triturated with petroleum ether. 53 g of a white substance, of melting point 104°–106° C., are obtained. The product has the following structure formula (active ingredient No. 3):

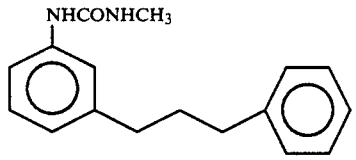

The following compounds can also be prepared in accordance with one of the above processes:

| No. | $\begin{array}{c} R^1 \\ N \\ R^2 \end{array}$ | Y | A | $(Z)_n$ | M.p. °C. |
|---|---|---|---|---|---|
| 4 | NHCH$_3$ | H | 3-CH$_2$ | H | 153–154 |

-continued

| No. | N⟨R¹/R² | Y | A | (Z)ₙ | M.p. °C |
|---|---|---|---|---|---|
| 5 | " | H | 3(CH₂)₂ | H | |
| 6 | " | H | 4(CH₂)₃ | H | 107–110 |
| 7 | " | 3Cl | 4(CH₂)₃ | H | |
| 8 | N(CH₃)₂ | H | 3(CH₂)₃ | H | 106–108 |
| 9 | N(OCH₃)CH₃ | H | " | H | 60–63 |
| 10 | NHcycl.C₃H₅ | H | " | H | 113–115 |
| 11 | N(C₂H₅)₂ | H | " | H | 85–87 |
| 12 | N(C₂H₅)(nC₄H₉) | H | " | H | oil |
| 13 | NHC₂H₅ | H | " | H | 83–85 |
| 14 |  | H | " | H | 88–90 |
| 15 |  | H | " | H | 112–114 |
| 16 |  | H | " | H | 111–113 |
| 17 | N(CH₃)cycl.C₆H₁₁ | H | " | H | 135–137 |
| 18 | NHCH₂CH₂Cl | H | " | H | |
| 19 | NHisoC₃H₇ | H | " | H | |
| 20 | NHCH₂CH₂OCH₃ | H | " | H | |
| 21 | NHCH₂CH₂CN | H | " | H | |
| 22 | NHCH₃ | H | " | 3OCH₃ | 84–85 |
| 23 | " | H | " | 4Cl | 147–148 |
| 24 | " | H | " | 3NHCONHCH₃ | |
| 25 | " | 4OCH₃ | " | 4SCN | |
| 26 | " | " | " | 4CH₂OCH₃ | |
| 27 | " | 4CH₃ | 3(CH₂)₃ | 3CN | |
| 28 | " | " | " | 4cyclC₅H₉ | |
| 29 | " | H | 3(CH₂)₄ | H | |
| 30 | " | " | " | 4CH₂C₆H₅ | |
| 31 | " | 4Cl | 3(CH₂)₃ | H | |
| 32 | N(CH₃)₂ | 4Cl | " | H | |
| 33 | NHCH₃ | H | " | 4-tert.C₄H₉ | 123–125 |
| 34 | " | " | " | 3Br | |
| 35 | " | " | " | 3OisoC₃H₇ | |
| 36 | " | " | " | 3OC₂H₄ | |
| 37 | " | " | " | 4OCH₃ | |
| 38 | " | " | " | 4F | 129–130 |
| 39 | " | " | " | 3OCHF₂ | |
| 40 | " | " | " | 4SCH₃ | |
| 41 | " | " | " | 4N(CH₃)₂ | |
| 42 | " | " | " | 3,4Cl₂ | |
| 43 | " | " | " | 2,5Cl₂ | |
| 44 | " | " | " | 2,4Cl₂ | |
| 45 | " | " | " | 2,4(CH₃)₂ | |
| 46 | " | " | " | 4C₆H₅ | 156–158 |
| 47 | " | " | " | 3CH₃ | 104–105 |
| 48 | " | " | " | 4CH₃ | 124–125 |
| 49 | " | " | " | 4Br | |
| 50 | " | " | 3(CH₂)₃ | 3COOC₂H₅ | |
| 51 | " | " | " | 3Cl | |
| 52 | NHCH₃ | H | 3(CH₂)₃ | 2Cl | |
| 53 | " | " | " | 2CH₃ | |
| 54 | " | " | " | 2OCH₃ | |
| 55 | " | " | " | 2,3(CH=CH—CH=CH) | |
| 56 | " | " | " | 3CF₃ | 125–126 |
| 57 | " | " | 3CH₂CH(CH₃)CH₂ | H | 82–84 |
| 58 | " | " | " | 4F | |
| 59 | " | " | 3(CH₂)₃CH(CH₃)CH₂ | H | oil |
| 60 | " | " | 3CH₂CH(C₂H₅)CH₂ | H | oil |
| 61 | N(CH₃)₂ | " | 3(CH₂)₃ | 2Cl | |
| 62 | " | " | " | 3Cl | |
| 63 | " | " | " | 4Cl | |
| 64 | N(CH₃)₂ | H | 3(CH₂)₃ | 2,4Cl₂ | |
| 65 | " | " | " | 2,5Cl₂ | |

-continued

| No. | N(R¹)(R²) | Y | A | (Z)ₙ | M.p. °C. |
|---|---|---|---|---|---|
| 66 | " | " | " | 3,4Cl₂ | |
| 67 | " | " | " | 2CH₃ | |
| 68 | " | " | " | 3CH₃ | |
| 69 | " | " | " | 4CH₃ | |
| 70 | " | " | " | 2,4(CH₃)₂ | |
| 71 | " | " | " | 3,4(CH₃)₂ | |
| 72 | " | " | " | 3OCH₃ | |
| 73 | " | " | " | 4OCH₃ | |
| 74 | " | " | " | 3OisoC₃H₇ | |
| 75 | " | " | " | 4C₂H₅ | |
| 76 | " | " | " | 4C₆H₅ | |
| 77 | " | " | " | 3CF₃ | |
| 78 | " | " | " | 4Br | |
| 79 | N(OCH₃)CH₃ | " | " | 2Cl | |
| 80 | " | " | " | 3Cl | 46–48 |
| 81 | " | " | " | 2,4Cl₂ | |
| 82 | " | " | " | 3,4Cl₂ | 54–56 |
| 83 | " | " | " | 2,5Cl₂ | |
| 84 | N(OCH₃)CH₃ | H | 3(CH₂)₃ | 2CH₃ | 88–90 |
| 85 | " | " | " | 3CH₃ | |
| 86 | " | " | " | 4CH₃ | 68–71 |
| 87 | " | " | " | 2,4(CH₃)₂ | |
| 88 | " | " | " | 3,4(CH₂)₃ | |
| 89 | " | " | " | 3OCH₃ | 76–77 |
| 90 | " | " | " | 4OCH₃ | |
| 91 | " | " | " | 4C₆H₅ | |
| 92 | " | " | " | 3CF₃ | |
| 93 | " | " | " | 2,3(CH=CH—CH=CH) | 93–95 |
| 94 | " | " | 4(CH₂)₃ | 4CH₃ | 58–60 |
| 95 | N(CH₃)₂ | " | " | " | 138–139 |
| 96 | N(CH₃)₂ | 3Cl | " | " | |
| 97 | NHCH₃ | H | 3(CH₂)₃ | 4C₂H₅ | 109–111 |
| 98 | " | " | " | 3OH | 80–82 |
| 99 | " | 4Br | " | H | 156–158 |
| 100 | N(CH₃)(OCH₃) | " | 3-CH₂—CH₂—CH₂— | " | 72–74 |
| 101 | " | H | " | 4-OC₂H₅ | 55–57 |
| 102 | " | " | " | 3-OCF₂CHF₂ | oil |
| 103 | " | " | " | 3,4-CH=CH—CH=CH— | |
| 104 | NHCH₃ | " | " | 4-OC₂H₅ | 93–95 |
| 105 |  (3-ethylpyrrolidin-1-yl) | " | " | H | 65–67 |
| 106 | 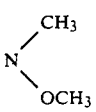 (3-methylmorpholin-4-yl) | " | " | " | 90–92 |
| 107 | —NHCH₃ | " | 4-CH₂—CH₂—CH₂— | 4-CH₃ | 139–142 |
| 108 | —N(CH₃)(OCH₃) | " | " | H | oil |
| 109 | " | " | 3-CH₂—CH₂—CH₂— | 3O—C₆H₅ 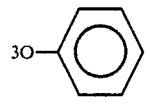 | oil |

| No. | N(R¹)(R²) | Y | A | (Z)ₙ | M.p. °C. |
|---|---|---|---|---|---|
| 110 | N(OCH₃)(CH₃) | H | 4CH₂CH₂CH₂ | 4F | 92–94 |
| 111 | " | " | " | 4O-tert.Butyl | |
| 112 | " | " | " | 4C₂H₅ | |
| 113 | " | " | " | 4-tert.Butyl | |
| 114 | " | " | " | 4Cl | 76–77 |
| 115 | " | " | " | 4NHCOCH₃ | |
| 116 | " | " | " | 4N(C₂H₅)₂ | |
| 117 | " | " | " | 4N(CH₃)₂ | 59–61 |
| 118 | " | " | " | 4OC₆H₁₃ | |
| 119 | " | " | " | 2Cl | |
| 120 | " | " | " | 3Cl | |
| 121 | " | " | " | 4-isopropyl | oil |
| 122 | " | " | " | 3-phenoxy | oil |
| 123 | " | " | " | 4-phenyl | 82–84 |
| 124 | " | " | " | 3OC₂H₅ | |
| 125 | " | " | " | 2CH₃ | oil |
| 126 | " | " | " | 3CH₃ | 40 |
| 127 | " | " | " | 2CF₃ | |
| 128 | " | " | " | 3CF₃ | 63–65 |
| 129 | " | " | " | 4CF₃ | |
| 130 | " | " | " | 2OCH₃ | |
| 131 | " | " | " | 3OCH₃ | 82–84 |
| 132 | " | " | " | 4OCH₃ | 68–70 |
| 133 | " | " | " | 2,4,6(CH₃)₃ | |
| 134 | " | " | " | 3,4Cl₂ | |
| 135 | " | " | " | 3OH | |
| 136 | " | " | " | 3OSO₂CH₃ | |
| 137 | N(OCH₃)(CH₃) | H | 4CH₂CH₂CH₂ | 2,4(CH₃)₂ | |
| 138 | " | " | " | 3OCH₂-phenyl | |
| 139 | " | " | " | 2F | |
| 140 | " | " | " | 4OC₂H₅ | |
| 141 | —N(pyrrolidine) | " | " | H | |
| 142 | —N(piperidine) | " | " | H | |
| 143 | —N(C₂H₅)₂ | " | " | H | |
| 144 | —N(thiomorpholine)S | " | " | H | |
| 145 | " | " | " | 4CH₃ | |
| 146 | " | " | " | 4F | |
| 147 | " | " | " | 4Cl | |
| 148 | —N(pyrrolidine) | " | " | 4CH₃ | 118–119 |
| 149 | " | " | " | 4F | |
| 150 | " | " | " | 4Cl | |
| 151 | NHC₂H₅ | " | " | 4CH₃ | |
| 152 | N(CH₃)₂ | " | " | " | |

-continued

| No. | N(R¹)(R²) | Y | A | (Z)ₙ | M.p. °C. |
|---|---|---|---|---|---|
| 153 |  | " | " | " | 104–106 |
| 154 | 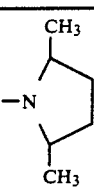 | " | " | " | 129–130 |
| 155 |  | " | " | " | 128–130 |
| 156 | $N(C_2H_5)_2$ | " | " | " | 70–72 |
| 157 | $NHOCH_3$ | " | " | " |  |
| 158 | $NHOC_2H_5$ | " | " | " |  |
| 159 | $NHCH_2CH{=}CH_2$ | " | " | " | 127–128 |
| 160 | $N(CH_3)C_4H_9$ | H | $4CH_2CH_2CH_2$ | $4CH_3$ | 75–76 |
| 161 | $NHC(CH_3)_2C{\equiv}CH$ | H | " | " |  |
| 162 | $N(CH_3)_2$ | " | " | 4Cl |  |
| 163 | " | " | " | 4F |  |
| 164 | " | " | " | $4OCH_3$" |  |
| 165 | $N(OCH_3)CH_3$ | " | $3CH_2CH_2CH_2$ |  | 98–100 |
| 166 | " | " | $4CH_2$ | H | 86–88 |
| 167 | " | " | " | 4-phenyl | 117–120 |
| 168 | " | $3CF_3$ | $4CH_2CH_2CH_2$ | H |  |
| 169 | " | H | $4(CH_2)_5$ | H |  |
| 170 | " | " | $4CH(CH_3)CH_2$ | H |  |
| 171 | " | " | $4CH_2CH(CH_3)$ | H |  |
| 172 | " | " | $4C(CH_3)_2$ | H |  |
| 173 | " | " | $4CH_2CH(C_3H_7)CH_2$ | H |  |
| 174 | " | " | " | $4OCH_3$ |  |
| 175 | " | " | $3(CH_2)_3CH(CH_3)CH_2$ | H | oil |
| 176 | " | " | $4(CH_2)_3CH(CH_3)CH_2$ | H |  |
| 177 | " | " | $4CH_2CH(C_2H_5)CH_2$ | H |  |
| 178 | " | " | " | $4CH_3$ |  |
| 179 | " | " | $3CH_2CH(CH_3)CH_2$ | 4F | oil |
| 180 | " | " | $4CH_2CH(CH_3)CH_2$ | H | 54–56 |
| 181 | " | " | " | $4CH_3$ | 67–69 |

-continued

| No. | $\begin{array}{c}R^1\\ \diagup\\ N\\ \diagdown\\ R^2\end{array}$ | Y | A | (Z)$_n$ | M.p. °C. |
|---|---|---|---|---|---|
| 182 | $\begin{array}{c}OCH_3\\ \diagup\\ N\\ \diagdown\\ CH_3\end{array}$ | H | 4CH$_2$CH—CH$_2$<br>    \|<br>    CH$_3$ | 4Cl | oil |
| 183 | " | " | 4CH$_2$CH—CH$_2$<br>    \|<br>    C$_4$H$_9$ | H | |
| 184 | " | " | 3CH$_2$—CH$_2$ | H | 100–103 |
| 185 | " | " | 4CH$_2$CH$_2$CH$_2$ | 3CO-phenyl | |
| 186 | " | H | " | 3,5-Cl$_2$4CH$_3$ | |
| 187 | " | " | " | 4NHCOCH$_3$ | |
| 188 | " | " | " | 4NHCOOC$_2$H$_5$ | |
| 189 | " | " | " | 4NHCO-phenyl | |
| 190 | " | " | " | 3CON(C$_2$H$_5$)$_2$ | |
| 191 | " | " | " | 3SO$_2$-phenyl | |
| 192 | " | " | " | 4COC$_2$H$_5$ | |
| 193 | " | " | " | 3SO$_2$N(CH$_3$)$_2$ | |
| 194 | " | " | 4CH$_2$CH$_2$ | H | 88–92 |
| 195 | " | " | 4CH$_2$CH$_2$CH$_2$CH$_2$ | H | 90–92 |
| 196 | " | " | 3CH$_2$CH$_2$CH$_2$CH$_2$ | H | 51 |
| 197 | N(CH$_3$)$_2$ | " | " | H | |
| 198 | " | " | 4CH$_2$CH$_2$CH$_2$CH$_2$ | H | |
| 199 | " | " | 3CH$_2$CH$_2$ | H | |
| 200 | " | " | 4CH$_2$ | H | |
| 201 | " | " | 4CH$_2$CH$_2$CH$_2$CH$_2$CH$_2$ | H | |
| 202 | " | " | 4CH—CH$_2$—CH<br>   \|         \|<br>  CH$_3$   CH$_3$ | H | |
| 203 | " | " | 3CH$_2$—C(CH$_3$)$_2$CH$_2$ | H | |
| 204 | " | " | 4CH$_2$C(CH$_3$)$_2$CH$_2$ | H | |

The novel active ingredients can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvent and/or carriers, with or without the addition of emulsifiers and dispersants and, where water is used as the diluent, with or without organic auxiliary solvents. Suitable auxiliaries are, essentially, solvents, for example aromatics, e.g., xylene and benzene, chloroaromatics, e.g. chlorobenze, paraffins, e.g. petroleum fractions, alcohols, e.g. methanol and butanol, amines e.g., ethanolamine, dimethylformamide, and water; solid carriers, for example natural rock powders, e.g., kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The agents in general contain from 0.1 to 95% by weight of active ingredient, preferably from 5 to 90%.

The agents, and the read-to-use preparations obtained therefrom, e.g., solutions, emulsions, suspensions, powders, dusts, pastes or granules, are applied in conventional manner, e.g. by spraying, atomizing, dusting, broadcasting or watering.

EXAMPLE I 90 parts by weight of compound 1 is mixed with 10 parts by weight of N-methyl-α-pyrrolidone. A mixture is obtained which is suitable for application in the form of very fine drops.

EXAMPLE II 10 parts by weight of compound 2 is dissolved in a mixture consisting of 90 parts by weight of xylene, 6 parts by weight of the adduct of 8 to 10 moles of ethylene oxide to 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

EXAMPLE III 20 parts by weight of compound 2 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

EXAMPLE IV 20 parts by weight of compound 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil.

EXAMPLE V 80 parts by weight of compound 1 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill.

EXAMPLE VI 5 parts by weight of compound 1 is intimately mixed with 95 parts by weight of particulate kaolin. A dust is obtained containing 5% by weight of the active ingredient.

EXAMPLE VII 30 parts by weight of compound 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE VIII 40 parts by weight of compound 1 is intimately mixed with 10 parts of the sodium salt of a phenolsulfonic acid-urea-formaldehyde condensate, 2 parts of silica gel and 48 parts of water. A stable, aqueous dispersion is obtained.

EXAMPLE IX 20 parts of compound 1 is intimately mixed with 12 parts of the calcium salt of dodecylbenzensulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The influence of various representatives of the novel aralkylphenylureas on the growth of unwanted and crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species.

In the preemergence treatment, the active ingredients were immediately applied to the surface of the soil as a suspension or emulsion in water by spraying through finely distributing nozzles. The amount of active ingredient applied in this treatment was equivalent to 3.0 kg/ha.

After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. For this treatment, either plants which had been sown directly in the pots and had grown there were selected, or plants which had been grown separately as seedlings and transplanted to the experiment vessels a few days before treatment. The amount of active ingredient applied in this treatment was equivalent to 0.25 kg/ha.

The comparative agent was 1-(3-(2-phenylethoxy)-phenyl)-3-methoxy-3-methylurea (A), applied at the same rates.

No cover was placed on the vessels in the postemergence treatment. The pots were set up in the greenhouse - species from warmer areas at from 20° to 30° C., and species from moderate climates at 15° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The results obtained show that new compound no. 2 is, on postemergence application in the greenhouse, tolerated by cereals better than prior art comparative agent (A). On preemergence application in the greenhouse, active ingredients 4, 8, 9, 14, 38, 47 and 57 have a herbicidal action which is mostly very good.

On postemergence application in the greenhouse, active ingredients 3 and 86 have, at a rate of 0.25 kg/ha, a better selective herbicidal action than prior art compound A. On postemergence application in the greenhouse, a good selective herbicidal action was exhibited by active ingredient no. 16 at 0.5 kg/ha, active ingredient no. 100 at 0.25 kg/ha and active ingredient no. 22 at 0.25 kg/ha. On postemergence application in the greenhouse, active ingredient no. 9 exhibited, at 0.25 kg/ha, a better selective herbicidal action than the prior art active ingredient 1-(3-(3-phenoxyethoxy)-phenyl)-3-methoxy-3-methylurea (B) (German Laid-Open Application DE-OS 2,846,723). On postemergence application in the greenhouse, active ingredient no. 8 exhibited, at 0.25 kg/ha, a better selective herbicidal action than the prior art active ingredient 1-(3-(2-phenoxyethoxy)-phenyl)-3,3-dimethylurea (C) (German Laid-Open Application DE-OS 2,846,723) at a rate of 2 kg/ha.

On postemergence treatment in the greenhouse, active ingredients nos. 84, 80, 102, 104, 101 and 109 exhibited, at 0.125 and 0.5 kg/ha, a better selective herbicidal action than the prior art active ingredient 1-(3-(2-(2,4-dichloro)-phenoxyethoxy)-phenyl)-3-methoxy-3-methylurea (D) (German Laid-Open Application DE-OS 2,846,723) at 0.5 kg/ha. On postemergence application in the greenhouse, active ingredient no. 94 exhibited, at 0.25 kg/ha, a better selective herbicidal action than prior art active ingredient 1-(4-(2-(4-methyl)-phenoxyethyl)-phenyl)-3-methoxy-3-methylurea (E) (German Laid-Open Application DE-OS 2,846,723).

If certain crop plants tolerate the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-direced, lay-by treatment).

In view of the good tolerance of the active ingredients and the many application methods possible, the agents according to the invention may be used in a large range of crops for removing unwanted plants.

Application rates may vary from 0.1 to 15 kg/ha and more.

The following crop plants may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel aralkylphenylureas may be mixed among themselves or mixed and applied together with numerous representatives of other herbicidal or growth-regulating active ingredient groups. Examples of suitable mixture components are diazines, benzothiadiazinones, 2,6-dinitroanilines, N-phenyl-caramates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

| | |
| --- | --- |
| methyl α-naphthoxyacetate | (salts, esters, amides) |
| 2-(2-methylphenoxy)-propionic acid | |
| 2-(4-chlorophenoxy)-propionic acid | (salts, esters, amides) |
| 2-(2,4-dichlorophenoxy)-propionic acid | (salts, esters, amides) |
| 2-(2,4,5-trichlorophenoxy)-propionic acid | (salts, esters, amides) |
| 2-(2-methyl-4-chlorophenoxy)-propionic acid | (salts, esters, amides) |
| 4-(2,4-dichlorophenoxy)-butyric acid | (salts, esters, amides) |
| 4-(2-methyl-4-chlorophenoxy)-butyric acid | (salts, esters, amides) |
| cyclohexyl-3-(2,4-dichlorophenoxy)-acrylate | |
| 9-hydroxyfluorenecarboxylic acid-(9) | (salts, esters) |
| 2,3,6-trichlorophenylacetic acid | (salts, esters) |
| 4-chloro-2-oxobenzothiazolin-3-yl-acetic acid | (salts, esters) |
| gibelleric acid | (salts) |
| disodium methylarsonate | |
| monosodium salt of methylarsonic acid | |
| N-phosphonomethyl-glycine | (salts) |
| N,N-bis-(phosphonomethyl)-glycine | (salts) |
| 2-chloroethyl 2-chloroethanephosphonate | |
| ammonium-ethyl-carbamoyl-phosphonate | |
| di-n-butyl-1-n-butylamino-cyclohexyl-phosphonate | |
| trithiobutylphosphite | |
| O,O-diisopropyl-5-(2-benzosulfonylaminoethyl)-phosphorodithionate | |
| 2,3-dihydro-5,6-dimethyl-1,4-dithiin-1,1,4,4-tetraoxide | |

| | |
|---|---|
| 5-tert.butyl-3-(2,4-dichloro-5-isopropoxyphenyl)-1,3,4-oxa-diazolone-(2) | |
| 4,5-dichloro-2-trifluoromethylbenzimidazole | (salts) |
| 1,2,3,6-tetrahydropyridazine-3,6-dione | (salts) |
| succinic acid mono-N-dimethylhydrazide | (salts) |
| (2-chloroethyl)-trimethylammonium chloride | |
| (2-methyl-4-phenylsulfonyl)-trifluoromethanesulfone anilide | |
| 1,1-dimethyl-4,6-diisopropyl-5-indanyl ethyl ketone | |
| sodium chlorate | |
| ammonium thiocyanate | |
| calcium cyanamide | |
| 5-amino-4-chloro-2-phenyl-3(2H)-pyridazinone | |
| 5-amino-4-bromo-2-phenyl-3(2H)-pyridazinone | |
| 5-amino-4-chloro-2-cyclohexyl-3(2H)-pyridazinone | |
| 5-amino-4-bromo-2-cyclohexyl-3(2H)-pyridazinone | |
| 5-methylamino-4-chloro-2-(3-trifluoromethylphenyl)-3(2H)-pyridazinone | |
| 5-methylamino-4-chloro-2-(3-α,α,β,β-tetrafluoroethoxyphenyl)-3(2H)-pyridazinone | |
| 5-dimethylamino-4-chloro-2-phenyl-3(2H)-pyridazinone | |
| 4,5-dimethoxy-2-phenyl-3(2H)-pyridazinone | |
| 4,5-dimethoxy-2-cyclohexyl-3(2H)-pyridazinone | |
| 4,5-dimethoxy-2-(3-trifluoromethylphenyl)-3(2H)-pyridazinone | |
| 5-methoxy-4-chloro-2-(3-trifluoromethylphenyl)-3(2H)-pyridazinone | |
| 5-amino-4-bromo-2(3-methylphenyl)-3(2H)-pyridazinone | |
| 3-(1-methylethyl)-1H-2,1,3-benzothiadiazin-4(3H)-one-2,2-dioxide and salts | |
| 3-(1-methylethyl)-8-chloro-1H-2,1,3-benzothiadiazin-4(3H)-one-2,2-dioxide and salts | |
| 3-(1-methylethyl)-8-fluoro-1H-2,1,3-benzothiadiazin-4(3H)-one-2,2-dioxide and salts | |
| 3-(1-methylethyl)-8-methyl-1H-2,1,3-benzothiadiazin-4(3H)-one-2,2-dioxide and salts | |
| 1-methoxymethyl-3-(1-methylethyl)-2,1,3-benzothiadiazin-4(3H)-one-2,2-dioxide | |
| 1-methoxymethyl-8-chloro-3-(1-methylethyl)-2,1,3-benzothiadiazin-4(3H)-one-2,2-dioxide | |
| 1-methoxymethyl-8-fluoro-3-(1-methylethyl)-2,1,3-benzothiadiazin-4(3H)-one-2,2-dioxide | |
| 1-cyano-8-chloro-3-(1-methylethyl)-2,1,3-benzothiadiazin-4(3H)-one-2,2-dioxide | |
| 1-cyano-8-fluoro-3-(1-methylethyl)-2,1,3-benzothiadiazin-4(3H)-one-2,2-dioxide | |
| 1-cyano-8-methyl-3-(1-methylethyl)-2,1,3-benzothiadiazin-4(3H)-one-2,2-dioxide | |
| 1-cyano-3-(1-methylethyl)-2,1,3-benzothiadiazin-4(3H)-one-2,2-dioxide | |
| 1-azidomethyl-3-(1-methylethyl)-2,1,3-benzothiadiazin-4(3H)-one-2,2-dioxide | |
| 3-(1-methylethyl)-1H-pyridino-[3,2-e]-2,1,3-thiadiazin-(4)-one-2,2-dioxide | |
| N-(1-ethylpropyl)-2,6-dinitro-3,4-dimethylaniline | |
| N-(1-methylethyl)-N-ethyl-2,6-dinitro-4-trifluoromethylaniline | |
| N-n-propyl-N-β-chloroethyl-2,6-dinitro-4-trifluoromethylaniline | |
| N-n-propyl-N-cyclopropylmethyl-2,6-dinitro-4-trifluoromethylaniline | |
| N-bis-(n-propyl)-2,6-dinitro-3-amino-4-trifluoromethylaniline | |
| N-bis-(n-propyl)-2,6-dinitro 4-methylaniline | |
| N-bis-(n-propyl)-2,6-dinitro-4-methylsulfonylaniline | |
| N-bis-(n-propyl)-2,6-dinitro-4-aminosulfonylaniline | |
| bis-(β-chloroethyl)-2,6-dinitro-4-methylaniline | |
| N-ethyl-N-(2-methylallyl)-2,6-dinitro-4-trifluoromethylaniline | |
| 3,4-dichlorobenzyl N-methylcarbamate | |
| 2,6-di-tert.butyl-4-methylphenyl N-methylcarbamate | |
| isopropyl N-phenylcarbamate | |
| 3-methoxyprop-2-yl N-3-fluorophenylcarbamate | |
| isopropyl N-3-chlorophenylcarbamate | |
| but-1-yn-3-yl N-3-chlorophenylcarbamate | |
| 4-chlorobut-2-yn-1-yl N-3-chlorophenylcarbamate | |
| methyl N-3,4-dichlorophenylcarbamate | |
| methyl N-(4-aminobenzenesulfonyl)-carbamate | |
| O-(N-phenylcarbamoyl)-propanone oxime | |
| N-ethyl-2-(phenylcarbamoyl)-oxypropionic acid amide | |
| 3'-N-isopropylcarbamoyloxypropionanilide | |
| ethyl-N-(3-(N'-phenylcarbamoyloxy)-phenyl)-carbamate | |
| methyl-N-(3-(N'-methyl-N'-phenylcarbamoyloxy)-phenyl)-carbamate | |
| isopropyl-N-(3-(N'-ethyl-N'-phenylcarbamoyloxy)-phenyl)-carbamate | |
| methyl-N-(3-(N'-3-methylphenylcarbamoyloxy)-phenyl)-carbamate | |
| methyl-N-(3-(N'-4-fluorophenylcarbamoyloxy)-phenyl)-carbamate | |
| methyl-N-(3-(N'-3-chloro-4-fluorophenylcarbamoyloxy)-phenyl)- | | carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil -continued 3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane  (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloro-acetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy-N-methoxyacetamide
2-( -naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyltrifluoromethanesulfone anilide
5-acetamido-4-methyltrifluoromethanesulfone anilide
2-propionylamino-4-methyl-5-chlorothiazole
O-(methylsulfonyl)-glycolic acid N-ethoxymethyl-2,6-dimethyl-anilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile  (salts)
3,5-diiodo-4-hydroxybenzonitrile  (salts)
3,5-dibromo-4-hydroxy-O-2,4-dinitrophenylbenzaldoxime  (salts)
3,5-dibromo-4-hydroxy-O-2-cyano-4-nitrophenylbenzaldoxime  (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitro-phenyl ether
2-chloro-4-trifluoromethylphenyl-3'-carboxy-4'-nitro-phenyl ether  (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1.0$^{2,6}$,0$^{8,11}$]-dodeca-3,9-diene -continued

| | |
|---|---|
| 2-ethoxy-2,3-dihydro-3,3-dimethyl-5-benzofuranylmethane sulfonate | |
| 2-ethoxy-2,3-dihydro-3,3-dimethyl-5-benzofuranyldimethylamino-sulfate | |
| 2-ethoxy-2,3-dihydro-3,3-dimethyl-5-benzofuranyl-(N-methyl-N-acetyl)-aminosulfonate | |
| 3,4-dichloro-1,2-benzisothiazole | |
| N-4-chlorophenyl-allylsuccinimide | |
| 2-methyl-4,6-dinitrophenol | (salts, esters) |
| 2-sec.butyl-4,6-dinitrophenol | (salts, esters) |
| 2-sec.butyl-4,6-dinitrophenol acetate | |
| 2-tert.butyl-4,6-dinitrophenol acetate | |
| 2-tert.butyl-4,6-dinitrophenol | (salts) |
| 2-tert.butyl-5-methyl-4,6-dinitrophenol | (salts) |
| 2-tert.butyl-5-methyl-4,6-dinitrophenol acetate | |
| 2-sec.amyl-4,6-dinitrophenol | (salts, esters) |
| 1-(α,α-dimethylbenzyl)-3-(4-methylphenyl)-urea | |
| 1-phenyl-3-(2-methylcyclohexyl)-urea | |
| 1-phenyl-1-benzoyl-3,3-dimethylurea | |
| 1-(4-chlorophenyl)-1-benzoyl-3,3-dimethylurea | |
| 1-(4-chlorophenyl)-3,3-dimethylurea | |
| 1-(4-chlorophenyl)-3-methyl-3-but-1-yn-3-yl-urea | |
| 1-(3,4-dichlorophenyl)-3,3-dimethylurea | |
| 1-(3,4-dichlorophenyl)-1-benzoyl-3,3-dimethylurea | |
| 1-(3,4-dichlorophenyl)-3-methyl-3-n.butylurea | |
| 1-(4-isopropylphenyl)-3,3-dimethylurea | |
| 1-(3-trifluoromethylphenyl)-3,3-dimethylurea | |
| 1-(3-α,α,β,β-tetrafluoroethoxyphenyl)-3,3-dimethylurea | |
| 1-(3-tert.butylcarbamoyloxyphenyl)-3,3-dimethylurea | |
| 1-(3-chloro-4-methylphenyl)-3,3-dimethylurea | |
| 1-(3-chloro-4-methoxyphenyl)-3,3-dimethylurea | |
| 1-(3,5-dichloro-4-methoxyphenyl)-3,3-dimethylurea | |
| 1-[4-(4'-chlorophenoxy)-phenyl]-3,3-dimethylurea | |
| 1-[4-(4'-methoxyphenoxy)-phenyl]-3,3-dimethylurea | |
| 1-cyclooctyl-3,3-dimethylurea | |
| 1-(hexahydro-4,7-methanoindan-5-yl)-3,3-dimethylurea | |
| 1-[1- or 2-(3a,4,5,7,7a-hexahydro)-4,7-methanoindanyl]-3,3-dimethylurea | |
| 1-(4-fluorophenyl)-3-carboxymethoxy-3-methylurea | |
| 1-phenyl-3-methyl-3-methoxyurea | |
| 1-(4-chlorophenyl)-3-methyl-3-methoxyurea | |
| 1-(4-bromophenyl)-3-methyl-3-methoxyurea | |
| 1-(3,4-dichlorophenyl)-3-methyl-3-methoxyurea | |
| 1-(3-chloro-4-bromophenyl)-3-methyl-3-methoxyurea | |
| 1-(3-chloro-4-isopropylphenyl)-3-methyl-3-methoxyurea | |
| 1-(3-chloro-4-methoxyphenyl)-3-methyl-3-methoxyurea | |
| 1-(3-tert.butylphenyl)-3-methyl-3-methoxyurea | |
| 1-(2-benzthiazolyl)-1,3-dimethylurea | |
| 1-(2-benzthiazolyl)-3-methylurea | |
| 1-(5-trifluoromethyl-1,3,4-thiadiazolyl)-1,3-dimethylurea | |
| imidazolidin-2-one-1-carboxylic acid isobutylamide | |
| 1,2-dimethyl-3,5-diphenylpyrazolium-methylsulfate | |
| 1,2,4-trimethyl-3,5-diphenylpyrazolium-methylsulfate | |
| 1,2-dimethyl-4-bromo-3,5-diphenylpyrazolium-methylsulfate | |
| 1,3-dimethyl-4-(3,4-dichlorobenzoyl)-5-(4-methylphenylsulfonyloxy)-pyrazole | |
| 2,3,5-trichloropyridinol-(4) | |
| 1-methyl-3-phenyl-5-(3'-trifluoromethylphenyl)-pyridone-(4) | |
| 1-methyl-4-phenylpyridinium chloride | |
| 1,1-dimethylpyridinium chloride | |
| 3-phenyl-4-hydroxy-6-chloropyridazine | |
| 1,1'-dimethyl-4,4'-dipyridylium-di(methylsulfate) | |
| 1,1'-di-(3,5-dimethylmorpholine-carbonylmethyl)-4,4'-dipyridylium dichloride | |
| 1,1'-ethylene-2,2'-dipyridylium dibromide | |
| 3-[1-(N-ethoxyamino)-propylidene]-6-ethyl-3,4-dihydro-2H-pyran-2,4-dione | |
| 3-[1-(N-allyloxyamino)-propylidene]-6-ethyl-3,4-dihydro-2H-pyran-2,4-dione | |
| 2-[1-(N-allyloxyamino)-propylidene]-5,5-dimethylcyclohexane-1,3-,dione | (salts) |
| 2-[1-(N-allyloxyamino-butylidene]-5,5-dimethylcyclohexane-1,3-dione | (salts) |
| 2-[1-(N-allyloxyamino-butylidene]-5,5-dimethyl-4-methoxycarbonyl-cyclohexane-1,3-dione | (salts) |
| 2-chlorophenoxyacetic acid | (salts, esters, amides) |
| 4-chlorophenoxyacetic acid | (salts, esters, amides) |
| 2,4-dichlorophenoxyacetic acid | (salts, esters, amides) |
| 2,4,5-trichlorophenoxyacetic acid | (salts, esters, amides) |
| 2-methyl-4-chlorophenoxyacetic acid | (salts, esters, amides) |
| 3,5,6-trichloro-2-pyridinyl-oxyacetic acid | (salts, esters, amides) |
| 2-chloro-4-trifluoromethyl-3'-ethoxycarbonyl-4'-nitrophenyl ether | |

-continued 1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy] -propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxycyclohex-2-en-1-one  (salts)
2-[1-(N-ethoxamino)-butylidene]-5-(2-phenylthiopropyl)-3-hydroxycyclohex-2-en-1-one  (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4'-nitrophenyl ether  (salts)
4,5-dimethoxy-2-(3-α,α,β-trifluoro-β-bromoethoxyphenyl)-3-(2H)-pyridazinone
2,4-dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1-(4-[2-(4-methylphenyl)-ethoxy]-phenyl-3-methyl-3-methoxyurea.

It may also be useful to apply the active ingredients, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. An aralkylphenylurea of the formula

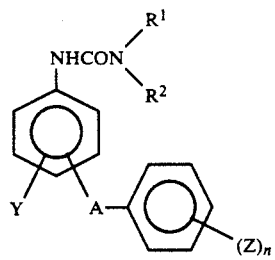

where $R^1$ and $R^2$ are alkoxy or unsubstituted or halogen- or cyano-substituted alkyl, cycloalkyl, alkenyl or alkynyl, or $R^1$ and $R^2$ together are unsubstituted or alkyl-substituted alkylene which may or may not be interrupted by oxygen or sulfur, Y is hydrogen, alkyl, halogen, alkoxy or haloalkyl, A is unsubstituted or alkyl-substituted alkylene, Z is alkyl, haloalkyl, alkoxyalkyl, cycloalkyl, aralkyl, aryl, aryloxy, halogen, a $C_4H_4$ chain which is fused to the benzene ring to give a substituted or unsubstituted naphthyl ring, alkoxy, haloalkoxy, alkylthio, thiocyanato, cyano,

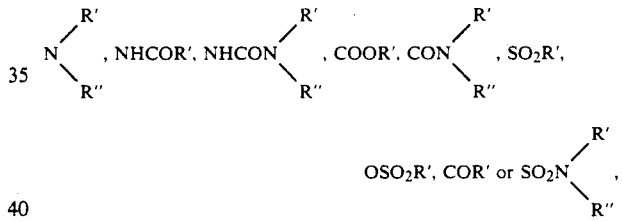

$R'$ and $R''$ being hydrogen, alkyl, alkoxy, alkylthio, cycloalkyl or unsubstituted or alkyl-, halogen or alkoxy-substituted phenyl and n is 1, 2, 3 or 4, with the proviso that where 1) A is n-propylene or n-butylene, 2) $R^1$ is methyl, 3) Y is hydrogen or chlorine, 4) Z is alkyl of 1 to 4 carbon atoms, and 5) n is 1, $R^2$ cannot be methyl or methoxy.

2. A process for combating the growth of unwanted plants, wherein the plants or the soil are treated with an effective herbicidal amount of an aralkylphenylurea of the formula

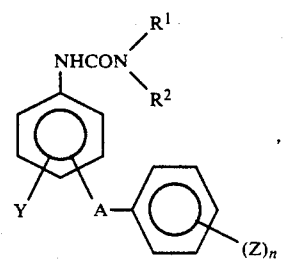

where $R^1$ and $R^2$ are hydrogen, alkoxy or unsubstituted or halogen-, alkoxy- or cyano-substituted alkyl, cycloalkyl, alkenyl or alkynyl, or $R^1$ and $R^2$ together are unsubstituted or alkyl-substituted alkylene which may or may not be interrupted by oxygen or sulfur, Y is hydrogen, alkyl, halogen, alkoxy or haloalkyl, A is unsubstituted or alkyl-substituted alkylene, Z is hydrogen, alkyl, haloalkyl, alkoxyalkyl, cycloalkyl, aralkyl, aryl, aryloxy, halogen, a C$_4$H$_4$ chain which is fused to the benzene ring to give a substituted or unsubstituted naphthyl ring, alkoxy, haloalkoxy, alkylthio, thiocyanato,

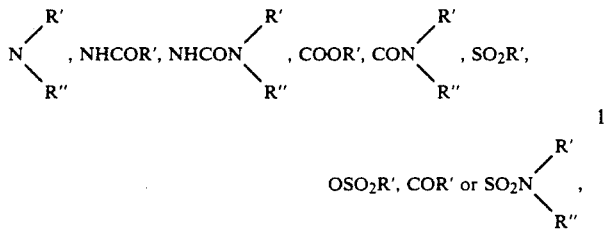

R' and R" being hydrogen, alkyl, alkoxy, alkylthio, cycloalkyl or unsubstituted or alkyl-, halogen- or alkoxy-substituted phenyl and n is 1, 2, 3 or 4, with the proviso that where 1) A is n-propylene of n-butylene, 2) R$^1$ is methyl, 3) Y is hydrogen or chlorine, 4) Z is hydrogen or alkyl of 1 to 4 carbon atoms, and 5) n is 1, R$^2$ cannot be methyl or methoxy.

3. A compound as set forth in claim 1, selected from the group consisting of
   N'-3-(3-(4-chlorophenyl)-propyl)-phenyl-N-methoxy-N-methylurea,
   N'-3-(3-(3-chlorophenyl)-propyl)-phenyl-N-methoxy-N-methylurea and
   N'-3-(3-(3,4-dichlorophenyl)-propyl)-phenyl-N-methoxy-N-methylurea.

4. A herbicidal composition comprising a carrier and/or diluent and from 0.1 to 95% by weight of an alkylphenylurea as defined in claim 1.

5. A herbicidal composition comprising a carrier and/or diluent and from 0.1 to 95% by weight of an alkylphenylurea as defined in claim 3.

6. A compound as set forth in claim 1, selected from the group consisting of:
   N'-3-(3-(3-trifluoromethylphenyl)-propyl)-phenyl-N-methyl-N-methoxyurea, and
   N'-4-(3-(3-trifluoromethylphenyl)-propyl)-phenyl-N-methyl-N-methoxyurea.

7. A herbicidal composition comprising a carrier and/or diluent and from 0.1 to 95% by weight of an aralkylphenylurea as defined in claim 6.

* * * * *

UNITED STATES PATENT AND TRADEMARK OFFICE
CERTIFICATE OF CORRECTION

PATENT NO. : 5,015,762
DATED : May 14, 1991
INVENTOR(S) : Ulrich SCHIRMER et al.

It is certified that error appears in the above-identified patent and that said Letters Patent is hereby corrected as shown below:

On the title page:

That part reading "3020969" should read -- 3020869 --

Claim 1, col 30, line 43

That part reading "alkyl-, halogen or al-"

should read --alkyl-, halogen- or al- --

Signed and Sealed this

Twenty-seventh Day of October, 1992

*Attest:*

DOUGLAS B. COMER

*Attesting Officer*   *Acting Commissioner of Patents and Trademarks*